United States Patent [19]

Helliwell et al.

[11] Patent Number: 5,422,280

[45] Date of Patent: Jun. 6, 1995

[54] METHOD FOR DETECTING DETERGENT COMPOSITIONS FOR ENHANCED SILICONE DEPOSITION COMPRISING SILICONE AND CATIONIC POLYMERS

[75] Inventors: John F. Helliwell, Merseyside, United Kingdom; Barbara Y. McFarquhar, Teaneck; Virgilio Villa, Bergenfield, both of N.J.

[73] Assignee: Lever Brothers Company, Division of Conopco, Inc., New York, N.Y.

[21] Appl. No.: 103,463

[22] Filed: Aug. 6, 1993

[30] Foreign Application Priority Data

Aug. 7, 1992 [GB] United Kingdom ................ 9216766

[51] Int. Cl.⁶ ................ G01N 31/02; C11D 1/62; C11D 1/65; C11D 1/88
[52] U.S. Cl. ................ 436/72; 252/547; 252/544; 252/545; 252/546; 252/174.15; 252/174.23; 252/174.24; 252/DIG. 13; 252/DIG. 14; 252/DIG. 7; 252/DIG. 2; 252/528; 252/174.17; 424/70.13; 424/70.15; 424/70.17
[58] Field of Search ......... 252/547, DIG. 13, 174.15, 252/174.23, 174.24, 544, 545, 546, DIG. 14, DIG. 7, DIG. 2, 528, 174.17; 424/70; 436/72

[56] References Cited

U.S. PATENT DOCUMENTS

| 3,723,325 | 3/1973 | Parran, Jr. ................ 252/547 X |
| 4,438,095 | 3/1984 | Grollier et al. ................ 424/70 |
| 4,529,586 | 7/1985 | De Marco et al. ................ 424/70 |
| 4,559,227 | 12/1985 | Chandra et al. ................ 424/70 |
| 4,592,859 | 6/1986 | Smith-Johannsen ................ 252/309 |
| 4,673,525 | 6/1987 | Small et al. ................ 252/132 |
| 4,673,568 | 6/1987 | Grollier et al. ................ 424/70 X |
| 4,812,253 | 3/1989 | Small et al. ................ 252/132 |
| 4,976,952 | 12/1990 | Lang et al. ................ 424/70 X |
| 5,006,263 | 4/1991 | Robinson et al. ................ 210/728 |
| 5,085,857 | 2/1992 | Reid et al. ................ 424/70 |
| 5,096,608 | 3/1992 | Small et al. ................ 252/132 |
| 5,182,105 | 1/1993 | Takata et al. ................ 424/70 X |

FOREIGN PATENT DOCUMENTS

| 308189 | 3/1989 | European Pat. Off. . |
| 308190 | 3/1989 | European Pat. Off. . |
| 3081400 | 4/1991 | Japan . |
| 2161172 | 1/1986 | United Kingdom . |

OTHER PUBLICATIONS

Kirk-Othmer, *Concise Encyclopedia of Chemical Technology*, John Wiley & Sons, 1985, pp. 492–494.

*Primary Examiner*—Paul Lieberman
*Assistant Examiner*—Douglas J. McGinty
*Attorney, Agent, or Firm*—Ronald A. Koatz

[57] ABSTRACT

This invention involves a method for determining silicone deposition enhancing cationic polymers to be formulated into silicone-containing formulations which comprises the steps of preparing a composition having an anionic surfactant, an amphoteric surfactant, silicone, and a cationic polymer, diluting that composition, and making a positive determination if flocculation occurs within three days.

1 Claim, No Drawings

METHOD FOR DETECTING DETERGENT COMPOSITIONS FOR ENHANCED SILICONE DEPOSITION COMPRISING SILICONE AND CATIONIC POLYMERS

BACKGROUND OF THE INVENTION

1. Field of the Invention

The present invention relates to detergent compositions, particularly bath and shower gel compositions, comprising silicone and cationic polymers, and to a method of predicting in which surfactant systems the cationic polymer will enhance silicone deposition.

2. Background of the Invention

A number of detergent compositions use cellulosic cationic polymers, for example, cationic guar gum derivatives.

Thus, for example, European Publication No. 0,203,750 (Small et al.) teaches skin cleansing bars comprising synthetic surfactants and "skin feel and mildness aids" such as the cationic polymer Polymer JR-400 (glycidyl trimethylammonium chloride ether of hydroxyethylcellulose). Although moisturizers/emollients are also included to provide skin conditioning benefits, there is no mention of a silicone oil.

EP 308,190 and EP 308,189 also teach bars comprising cationic polymers and a benefit reagent such as a moisturizer. Neither reference teaches the use of cationic polymer with silicone, nor does it teach a predictive method of determining in which active systems silicone deposition would be enhanced.

GB 2,161,172 teaches a shampoo composition which comprises a quaternized polymer (e.g., quaternized guar gum) and an organofunctional silicone. The reference fails to teach a predictive method for enhanced silicone deposition.

In addition, EP 117,135 (Johnson & Johnson), DE 3,305,318 (L'Oreal), J54015912 (Lion) and BE 864,863 (L'Oreal) each teach cleanser compositions with a cationic polymer and a benefit reagent. None of the references, however, teach cationic polymer in combination with silicone, let alone the specific active systems of the invention.

JP 3-81400 (Toky Beauty KK) teaches compositions comprising both silicone oil and cellulosic cationic polymers. However, there is no teaching or suggestion from this reference that silicone deposition is enhanced in certain active compositions while not in others, and no predictive method for ascertaining in which compositional environment silicone deposition would be enhanced.

EP 432,951 teaches compositions comprising cationic polymer and silicone and mentions silicone deposition. Again, however, there is no teaching of a predictive method for identifying when silicone deposition will occur.

U.S. Pat. No. 3,723,325 to Parran, Jr. et al. teaches compositions containing particle deposition enhancing agents. Among the cationic polymers which may be used to enhance deposition are nitrogen substituted cellulose ether derivatives. However, there is no specific mention of using these polymers to enhance deposition of silicone and the reference appears to be more related to depositing antimicrobial agents.

Moreover, it is said that the cationic polymers may be used in just about any active-containing composition (see column 3, lines 11-13) and there is no recognition that silicone may be deposited more readily in some environments than other, and no predictive method established for determining what these environments might be.

Accordingly there is a need in the art both for determining in which compositions enhanced silicone deposition can be found and for determining a methodology for finding these compositions.

SUMMARY OF THE INVENTION

By this invention, applicants have unexpectedly discovered a method for determining in which compositions the use of a cationic polymer will enhance deposition of silicone. Specifically, applicants have discovered that there is a direct correspondence between enhanced flocculation and/or creaming of silicone droplets in diluted product at user concentration (5 to 20%) and enhanced deposition of silicone (providing in turn enhanced skin feel effect). That is, by determining in which detergent active-containing compositions enhanced flocculation/creaming occurs, one can determine in which detergent active-containing compositions enhanced silicone deposition will also occur.

Accordingly, the present invention provides a method for enhancing deposition of silicone in a silicone-containing detergent composition which method comprises:

(a) preparing an active-containing composition containing a cationic polymer;

(b) preparing a second active-containing composition identical to the first but without the cationic polymer;

(c) diluting each of said compositions with water;

(d) visually observing whether the diluted composition containing a polymer flocculates after three days; and (e) if the diluted composition with the cationic polymer does flocculate, utilizing this composition as a composition providing enhanced silicone deposition relative to other active-containing compositions.

Of course, it is understood that the compositions without the polymer does not flocculate upon observation after three days.

DETAILED DESCRIPTION OF THE INVENTION

The subject invention provides a method for predicting in which specific detergent-active systems a cationic polymer will provide enhanced silicone deposition.

Specifically, the invention provides a method which comprises:

(a) preparing a desired active-containing composition containing a cationic polymer (and, of course, silicone);

(b) preparing a second active-containing composition identical to the first except that it does not contain the cationic polymer;

(c) diluting each of said compositions with water;

(d) visually observing whether the first diluted composition containing polymer flocculates after three days; and (e) if the cationic containing diluted composition does flocculate, utilizing this composition as a composition providing enhanced silicone deposition relative to other active-containing compositions.

The invention further relates to compositions prepared utilizing the above-outlined methodology.

The detergent compositions of the subject invention are generally, though not necessarily, bath or gel compositions suitable for personal washing of hair or skin. It is generally desirable that such compositions be mild to the skin, yet able to generate lather which the user will judge to be good in both quantity and quality. As a rough rule, anionic detergent actives are better foaming, but harsher on skin, and nonionics are mild but low foaming. Zwitterionic actives are also often used.

In short, the shower gel or bath compositions can be formulated in a large number of ways. Prior to the subject invention, there was no teaching or suggestion that a cationic polymer in some detergent active systems would enhance silicone deposition better than in any other active systems, nor was there any method of predicting how to find the advantageous systems.

Typically, the compositions may contain relatively mild anionic and amphoteric surfactants. When formulating compositions to test for flocculation/silicone deposition enhancement, starting formulating materials may include anionic and amphoteric surfactants as well as nonionic surfactants.

One preferred anionic detergent is fatty acyl isethionate of formula:

RCO$_2$CH$_2$CH$_2$SO$_3$M where R is an alkyl or alkenyl group of 7 to 21 carbon atoms and M is a solubilizing carbon such as sodium, potassium ammonium or substituted ammonium. Preferably at least three quarters of the RCO groups have 12 to 18 carbon atoms and may be derived from coconut.

Another preferred anionic detergent is alkyl ether sulphate of formula:

RO(CH$_2$CH$_2$O)$_n$SO$_3$M where R is an alkyl group of 8 to 22 carbon atoms, n ranges from 0.5 to 10 especially 1.5 to 8, and M is a solubilizing cation as before.

Other possible anionic detergents include alkyl glyceryl ether sulphate, sulphosuccinates, taurates, sarcosinates, sulphoacetates, alkyl phosphates and acyl lactates. Sulphosuccinates may be monoalkyl sulphosuccinates having the formula:

R$^5$O$_2$CCH$_2$CH(SO$_3$M)CO$_2$M and amido-MEA sulphosuccinates of the formula:

R$^5$CONHCH$_2$CH$_2$O$_2$CCH$_2$CH(SO$_3$M)CO$_2$M wherein R$^5$ ranges from C$_8$–C$_{20}$ alkyl, preferably C$_{12}$–C$_{15}$ alkyl and M is a solubilizing cation.

Sarcosinates are generally indicated by the formula:

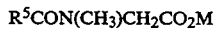
R$^5$CON(CH$_3$)CH$_2$CO$_2$M wherein R ranges from C$_8$–C$_{20}$ alkyl, preferably C$_{12}$–C$_{15}$ alkyl and M is a solubilizing cation.

Taurates are generally identified by the formula:

R$^5$CONR$^6$CH$_2$CH$_2$SO$_3$M wherein R$^5$ ranges from C$_8$–C$_{20}$ alkyl, preferably C$_{12}$–C$_{15}$ alkyl, R$^6$ ranges from C$_1$–C$_4$ alkyl, and M is a solubilizing cation.

The anionic detergent included in the composition will generally be selected to avoid harsh detergent such as primary alkane sulphonate or alkyl benzene sulphonate. The amount, if any, of these is preferably less than 3% of the detergents present.

Suitable zwitterionic detergents have a hydrophilic head group which contains both a quaternary nitrogen atom and at least one acid group which may be a carboxylic or a sulphonic acid group. Such detergents should generally include an alkyl or alkenyl group of 7 to 18 carbons atoms. They will usually comply with an overall structural formula

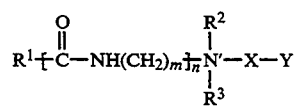
$$R^1\!-\!\!\overset{\overset{\displaystyle O}{\|}}{C}\!-\!NH(CH_2)_m\!\!\overline{\phantom{x}}_{\!n}\!\!\overset{\overset{\displaystyle R^2}{|}}{\underset{\underset{\displaystyle R^3}{|}}{N'}}\!-\!X\!-\!Y$$

where R$^1$ is alkyl or alkenyl of 7 to 18 carbon atoms, R$^2$ and R$^3$ are each independently alkyl, hydroxyalkyl or carboxyalkyl of 1 to 3 carbon atoms
m is 2 to 4
n is 0 or 1
X is alkylene of 1 to 3 carbon atoms optionally substituted with hydroxyl, and
Y is —CO$_2$ or —SO$_3$ Zwitterionic detergents within the above general formula include simple betaines of formula:

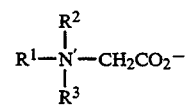
$$R^1\!-\!\!\overset{\overset{\displaystyle R^2}{|}}{\underset{\underset{\displaystyle R^3}{|}}{N'}}\!-\!CH_2CO_2^-$$

and amido betaines of formula:

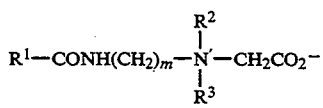
$$R^1\!-\!CONH(CH_2)_m\!-\!\!\overset{\overset{\displaystyle R^2}{|}}{\underset{\underset{\displaystyle R^3}{|}}{N'}}\!-\!CH_2CO_2^-$$

where m is 2 or 3.

In both formulae R$^1$, R$^2$ and R$^3$ are as defined previously. R$^1$ may in particular be a mixture of C$_{12}$ and C$_{14}$ alkyl groups derived from coconut so that at least half, preferably at least three quarters of the groups R$^1$ have 10 to 14 carbon atoms. R$^2$ and R$^3$ are preferably methyl.

A further possibility is that the zwitterionic detergent is a sulphobetaine of formula:

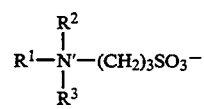
$$R^1\!-\!\!\overset{\overset{\displaystyle R^2}{|}}{\underset{\underset{\displaystyle R^3}{|}}{N'}}\!-\!(CH_2)_3SO_3^-$$

or

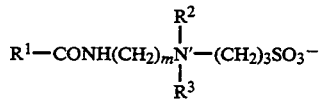
$$R^1\!-\!CONH(CH_2)_m\!\!\overset{\overset{\displaystyle R^2}{|}}{\underset{\underset{\displaystyle R^3}{|}}{N'}}\!-\!(CH_2)_3SO_3^-$$

where m is 2 or 3, or variants of these in which —(CH$_2$)$_3$SO$_3$ is replaced by

$$-CH_2\overset{\overset{\displaystyle OH}{|}}{C}HCH_2SO_3^-$$

$R^1$, $R^2$ and $R^3$ in these formulae are as defined previously.

The amphoteric betaines and sultaines are used as a co-surfactant. Nonionics may not be used as the sole surfactant in the formulated products because of their low foaming ability; however, they can be incorporated as a co-surfactant. A preferred betaine is cocoamidopropylbetaine. The surfactant and co-surfactant preferably have a ratio of 1:5 to 5:1.

Other anionic detergents beside acyl isethionate may be present notably in quantities from 10 to 50% of the detergent mixture. Anionic detergent which is particularly envisaged is alkyl ether sulphate of the formula:

R⁴O(CH₂CH₂O)$_t$ SO₃M where $R^4$ is alkyl or alkenyl of 8 to 18 carbon atoms, especially 11 to 15 carbon atoms, t has an average value of at least 2.0 and M is a solubilizing cation such as sodium, potassium, ammonium or substituted ammonium. Preferably t has an average value of 3 or more.

Alkanolamide detergents are preferably included at only a low level, if at all, since they have been found to reduce mildness. Preferably they are restricted to not more than 5% by weight of the detergent mixture. Even better is to exclude alkanolamides and the harsh anionics, alkyl benzene sulphonate and primary alkane sulphonate completely. It is also preferred that amine oxide is not more than 5% by weight of the detergent mixture, since this has been found to reduce lather quality.

Other surfactants which can be used are disclosed in U.S. Pat. No. 3,723,325 to Parran, Jr., et al., which is hereby incorporated by reference into the subject application. Surfactants will generally comprise 2% to 95% of the total composition, preferably 5 to 35%

In addition to the surfactant system, the cationic polymer (discussed below) and the silicone (discussed below), the compositions of the invention can also optionally contain moisturizers/emollients such as C₆–C₂₂ fatty acids at 0–40%, preferably 5–30% by weight; perfumes (at levels of 0.1–1.5%), colorants, fillers, preservatives and anti-bacterials.

In principle, the cationic polymers used in the process and compositions of the invention may be any polymer of the polyamine, polyaminoamide, or quaternary polyammonium type, with the amine or ammonium group constituting part of the polymer chain or being bonded thereto. Examples of these are any of the cationic polymers described in U.S. Pat. No. 4,438,095, hereby incorporated by reference into the subject application.

Preferred polymers are derivative of cellulose ethers entailing quaternary ammonium groupings such as those described in French Patent No. 1,492,597 such as, for example, polymers sold under the designation JR (e.g., JR 125, JR 400, JR 30M) and LR (e.g., LR 500 and LR 30M) by Union Carbide under the designation CELQUAT by National Starch Company; and cationic polysaccharides such as those described in U.S. Pat. No. 3,509,978 or U.S. Pat. No. 4,031,307, both of which are incorporated herein by reference.

Specific examples of cationic polymers which may be used in the invention are a glycidyltrimethylammonium chloride ether of hydroxyethylcellulose (Polymer JR-400, Union Carbide), a quaternary ammonium salt of a polyvinylpyrrollidone derivative (Gafcoat 734, GAF), polydimethylmethylenepyrellidinium chloride (Mercoat 100, Merck), a quaternary ammonium derivative of hydroxy propyl guar (Jaguar C-13-S, Meyhall), and a quaternary ammonium salt of hydrolyzed gelatin (Crodine Q, Croda).

The polymer will generally be used in the compositions of the invention in an amount ranging from about 0.01 to 2.0% by wt., preferably 0.05 to 0.5%

The silicone oil of the invention which will undergo enhanced deposition has the general formula.

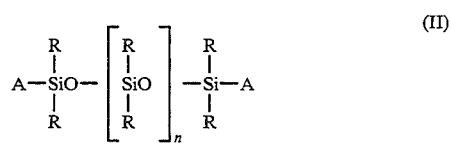

Other silicones suitable for use in the present invention include the cyclic silicones. These materials have the formula:

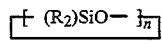

where n is 4 or 5 and R has the same meaning as in the structure of linear siloxanes.

The dimethyl cyclic siloxanes are volatile, and are thus present only temporarily after deposition. Volatile cyclic silicones are available under the trade name DOW CORNING 344 and 345 fluids from the Dow Corning Corporation.

Silicone used in this invention may well be a silicone homopolymer, although silicones may be modified by including copolymers, e.g., polyethers as is described in U.S. Pat. No. 3,957,970. Such copolymers tend to be more soluble than homopolymers of silicone.

The silicone component will generally comprise 0.1 to 15% by weight of the composition. Preferably, however, it will comprise greater than 1% of the composition.

Other materials may be included in compositions of this invention. Possibilities include coloring agents, opacifying agents, organic polymers, perfumes including deodorant perfumes, bactericidal agents to reduce the microflora on skin, antioxidants and other preservatives.

Typically, the cationic polymer of the invention is first dispersed in water. The anionic and amphoteric surfactants are then added with mixing. For formulations which contain isethionate, this ingredient is then added and the solution heated to about 160° F. until dissolved. As the solution cools, silicone, salt, perfume and other ingredients are added. Mixing may be continued for up to 30 minutes.

After the composition has been prepared (both with and without cationic polymer), the product is diluted anywhere from about 5 to 20 times weight for weight with water. Thus typically 0.5 gram, 1 gram and 2 gram quantities of product are diluted to 10 grams.

A typical composition might contain:
2–20% anionic surfactant
1–8% amphoteric
0.1–15% silicone
0.01–2% cationic polymer
perfume
preservatives
salt The invention will be further illustrated by means of the following examples which are not intended to be limiting in any way.

EXAMPLE 1

Determining Flocculation & Silicone Deposition

The flocculation measurements according to the subject invention consist of diluting products with and without cationic polymer to user concentrations to observe whether the polymer causes flocculation.

Specifically, 2, 1 and 0.5 g quantities of tested products, both with and without polymer, were diluted to 10 grams with distilled water in small stoppered tubes. The products were mixed thoroughly and have to stand for up to three (3) days to observe any visible sign of flocculation at room temperature.

In the absence of polymer, silicone droplets did not flocculate and because of their small size (about 0.5 microns), did not cream to the surface. In those cationic containing products where flocculation was observed, enhanced silicone deposition (most easily detected by creaming of silicone to the surface) was also observed.

Generally, silicone deposition may also be measured as follows:

The volar surface of the forearm is pre-washed with a product containing neither silicone nor polymer. A tape strip is removed to monitor the initial silicon and sulfur level on the skin. 30 minutes later, both the forearm and the hand is pre-wetted. 0.5 gm of test product is lathered on the forearm for 10 secs using the opposite pre-wetted hand. The arm is then rinsed for 10 sec under the tap, rubbing with the hand to ensure sufficient rinsing. A paper towel is passed over the arm in a single stroke. The arm is air dried for 10 minutes, a tape strip taken and the silicon/sulfur ratio determined by x-ray fluorescence spectroscopy. The silicon/sulfur ratio of the test product is compared with that of the control.

The tape used is a "J-Lar Superclear 1". It is applied to the skin for 30 secs using 85 g/cm pressure.

EXAMPLE 2

0.1% Jaguar was placed into active systems comprising
(a) 12% SLES-3EO; 3% cocobetaine; 1.5% NaCl;
(b) 13% SLES-2EO; 2% cocobetaine;
(c) 9% Fenopon AC78 and 6% cocobetaine;
(d) 5% Fenopon AC78, 8% CAPB; 2% SLES-3EO;
(e) 15% of a 1:1 mixture oleate/cocoate; and
(f) 12% of a 1:1 mixture oleate/cocoate; 3% cocobetaine SLES—3EO is sodium laureth ether sulfate (average 3 ethylene oxides/molecule)

SLES—2EO is sodium laureth ether sulfate (average 2 ethylene oxide/molecule)

Fenopon AC78 is sodium cocoyl isethionate

CAPB is cocamidopropylbetaine

The Jaguar caused flocculation in each of systems (a), (b), (c), (d) and (f) but caused no flocculation (by visual observation) in system (e). Since silicone deposition was found in each of systems (a), (b), (c), (d) and (f), it can be seen that there is a direct correlation between flocculation and systems having enhanced silicone deposition.

EXAMPLE 3

0.1% Polymer JR-400 was placed into active systems comprising:
(a) 12% SDS; 3% $C_{12}E_6$; 1% NaCl;
(b) 13% SLES-2EO; 2% cocobetaine;
(c) 15% SLES;
(d) 15% SDS SDS is sodium dodecyl (lauryl) sulfate SLES is sodium laureth sulfate Here, the Polymer JR-400 caused flocculation (upon visual observation after 3 days) in system (a), but none in system (b), (c) and (d). Again, since silicone deposition occurred only with system (a), it can be seen that there is a direct correlation between visual observation of flocculation and enhanced silicone deposition.

We claim:

1. A method for determining silicone deposition enhancing cationic polymers to be formulated into a silicone-containing formulation wherein said method comprises:
   (a) preparing a composition comprising:
      (1) 2 to 20% by wt. anionic surfactant;
      (2) 1 to 8% by wt. amphoteric surfactant;
      (3) 0.1 to 15% by wt. silicone; and
      (4) 0.01 to 2% by wt. cationic polymer selected from the group consisting of glycidyltrimethylammonium chloride ethers of hydroxyethylcellulose; quaternary ammonium salts of polyvinylpyrrollidone derivatives; polydimethylenepyrellidinium chlorides; quaternary ammonium derivatives of hydroxy propyl guar; and quaternary ammonium salts of hydrolyzed gelatin;
   (b) diluting said composition 5 to 20 times weight for weight with water in a container;
   (c) visually observing whether there has been flocculation in said container after three days; and
   (d) if the cationic polymer-containing diluted composition does flocculate, determining that said cationic polymer is a silicone deposition enhancing cationic polymer in said silicone-containing formulation.

* * * * *